US010835176B2

(12) United States Patent
Mohammadrezazadeh et al.

(10) Patent No.: US 10,835,176 B2
(45) Date of Patent: Nov. 17, 2020

(54) PERSONALIZED CLOSED-LOOP PULSED TRANSCRANIAL STIMULATION SYSTEM FOR COGNITIVE ENHANCEMENT

(71) Applicant: HRL Laboratories, LLC, Malibu, CA (US)

(72) Inventors: Iman Mohammadrezazadeh, Los Angeles, CA (US); Praveen K. Pilly, West Hills, CA (US); Michael D. Howard, Westlake Village, CA (US)

(73) Assignee: HRL Laboratories, LLC, Malibu, CA (US)

( * ) Notice: Subject to any disclaimer, the term of this patent is extended or adjusted under 35 U.S.C. 154(b) by 235 days.

(21) Appl. No.: 15/983,336

(22) Filed: May 18, 2018

(65) Prior Publication Data

US 2019/0021657 A1 Jan. 24, 2019

Related U.S. Application Data

(60) Provisional application No. 62/534,091, filed on Jul. 18, 2017.

(51) Int. Cl.
*A61N 1/00* (2006.01)
*A61B 5/00* (2006.01)
(Continued)

(52) U.S. Cl.
CPC .............. *A61B 5/4836* (2013.01); *A42B 1/04* (2013.01); *A61B 5/0476* (2013.01);
(Continued)

(58) Field of Classification Search
CPC ... A61B 5/4836; A61B 5/0476; A61B 5/6803; A61B 5/7485; A61B 5/0478;
(Continued)

(56) References Cited

U.S. PATENT DOCUMENTS

2011/0093033 A1 4/2011 Nekhendzy
2013/0096363 A1 4/2013 Schneider et al.
(Continued)

FOREIGN PATENT DOCUMENTS

KR 10-1114299 B1 3/2012

OTHER PUBLICATIONS

Jacek P .Dmochowski, LaurentKoessler, Anthony M.Norica, MaromBikson, Lucas C.Parra (2017). Optimal use of EEG recordings to target active brain areas with transcranial electrical stimulation. NeuroImage, vol. 157, pp. 69-80.
(Continued)

*Primary Examiner* — Scott M. Getzow
(74) *Attorney, Agent, or Firm* — Tope-McKay & Associates

(57) ABSTRACT

A system for closed-loop pulsed transcranial stimulation for cognitive enhancement. During operation, the system identifies a region of interest (ROI) in a subject's brain and then estimates ROI source activations based on the estimated source of the ROI. It is then determined if a subject is in a bad encoding state based on the ROI source activations. Finally, one or more electrodes are activated to apply a pulsed transcranial stimulation (tPS) therapy when the subject is in a bad encoding state, a predefined external event or behavior occurs, or the subject is in a consolidation state during sleep.

21 Claims, 10 Drawing Sheets

(51) Int. Cl.
| | |
|---|---|
| A61N 1/04 | (2006.01) |
| A42B 1/04 | (2006.01) |
| A61N 1/36 | (2006.01) |
| A61B 5/0478 | (2006.01) |
| A61N 1/02 | (2006.01) |
| A61B 5/0476 | (2006.01) |

(52) U.S. Cl.
CPC .......... *A61B 5/0478* (2013.01); *A61B 5/6803* (2013.01); *A61B 5/7485* (2013.01); *A61N 1/025* (2013.01); *A61N 1/0456* (2013.01); *A61N 1/0476* (2013.01); *A61N 1/0484* (2013.01); *A61N 1/36025* (2013.01); *A61N 1/36031* (2017.08); *A61B 2562/0209* (2013.01); *A61B 2562/046* (2013.01)

(58) Field of Classification Search
CPC ...... A61B 2562/0209; A61B 2562/046; A61N 1/36031; A61N 1/025; A61N 1/36025; A61N 1/0484; A61N 1/0476; A61N 1/0456; A42B 1/04
See application file for complete search history.

(56) References Cited

U.S. PATENT DOCUMENTS

| | | |
|---|---|---|
| 2015/0112409 A1 | 4/2015 | Hagedorn |
| 2015/0174418 A1 | 6/2015 | Tyler et al. |

OTHER PUBLICATIONS

Y Ezzyat, JE Kragel, JF Burke, DF Levy, A Lyalenko, P Wanda, et al (2017). Direct brain stimulation modulates encoding states and memory performance in humans. Current Biology 27 (9), pp. 1251-1258.

Matthew R. Krause, Theodoros P. Zanos, Bennett A. Csorba, Praveen K. Pilly, Jaehoon Choe, Matthew E. Phillips, Abhishek Datta, and Christopher C. Pack. Transcranial direct current stimulation facilitates associative learning and alters functional connectivity in the primate brain. Current Biology 27, pp. 1-11, Oct. 23, 2017.

Elsa Van Der Loo, Marco Congedo, Mark Plazier, Paul Van de Heyning, Dirk De Ridder. (2007). Correlation between Independent Components of scalp EEG and intra-cranial EEG (iEEG) time series. International Journal of Bioelectromagnetism, vol. 9, No. 4, pp. 270-275.

R. Hyder, N. Kamel, T. B. Tang and J. bornot, "Brain source localization techniques: Evaluation study using simulated EEG data," 2014 IEEE Conference on Biomedical Engineering and Sciences (IECBES), Kuala Lumpur, 2014, pp. 942-947.

Jasmine Song, Colin Davey, Catherine Poulsen, Phan Luu, Sergei Turovets, Erik Anderson, Kai Li, Don Tucker, EEG source localization: Sensor density and head surface coverage, Journal of Neuroscience Methods, vol. 256, 2015, pp. 9-21, ISSN 0165-0270.

A.M. Dale, M.I. Sereno. Improved localization of cortical activity by combining EEG and MEG with MRI cortical surface reconstruction: a linear approach, J Cognit Neurosci, 5 (1993), pp. 62-176.

R. Pascual-Marqui. Standardized low resolution brain electromagnetic tomography (sLORETA): technical details. Methods Find Clin Pharmacol, 24D (2002), pp. 5-12.

Munsif Ali Jatoi, Nidal Kamel, Aamir Saeed Malik, Ibrahima Faye, Tahamina Begum, A survey of methods used for source localization using EEG signals. Biomedical Signal Processing and Control, vol. 11, 2014, pp. 42-52, ISSN 1746-8094, https://doi.org/10.1016/j.bspc.2014.01.009.

Notification of Transmittal of International Search Report and the Written Opinion of the International Searching Authority for PCT/US2018/033354; dated May 9, 2019.

International Search Report of the International Searching Authority for PCT/US2018/033354; dated May 9, 2019.

Written Opinion of the International Searching Authority for PCT/US2018/033354; dated May 9, 2019.

Notification of and the International Preliminary Report on Patentability Chapter II for PCT/US2018/033354; dated Oct. 22, 2019.

PERSONALIZED CLOSED-LOOP PULSED TRANSCRANIAL STIMULATION SYSTEM FOR COGNITIVE ENHANCEMENT

CROSS-REFERENCE TO RELATED APPLICATIONS

This application claims the benefit of and is a non-provisional patent application of U.S. Provisional Application No. 62/534,091, filed on Jul. 18, 2017, the entirety of which is hereby incorporated by reference.

GOVERNMENT RIGHTS

This invention was made with government support under U.S. Government Contract Number N66001-16-C-4058 and N66001-16-C-4066, awarded by DARPA BTO. The government has certain rights in the invention.

BACKGROUND OF INVENTION

(1) Field of Invention

The present invention relates to a transcranial stimulation system and, more specifically, to a closed-loop pulsed transcranial stimulation system for cognitive enhancement.

(2) Description of Related Art

Transcranial stimulation techniques have been devised to solve a variety of cognitive issues. By way of Example, Ezzyat et al. provided a way to control stimulation based on brain state awareness provided by implanted electrodes in epilepsy patients (see the List of Incorporated Literature References, Literature Reference No. 2). Such electrodes only give data in the implanted areas and fail to operate in a closed-loop. In other words, existing techniques are unable to selectively apply stimulation only when it is most effective.

Thus, a continuing need exists for a system that provides a closed-loop and pulsed stimulation system that operates to effectively apply the stimulation montage at times which stimulate is most effective in cognitive enhancement.

SUMMARY OF INVENTION

This disclosure provides a system for closed-loop pulsed transcranial stimulation for cognitive enhancement. In some embodiments, the system includes a headcap having a plurality of electrodes and one or more processors and a memory. The memory is a non-transitory computer-readable medium having executable instructions encoded thereon, such that upon execution of the instructions, the one or more processors perform several operations. For example, during operation, the system identifies a region of interest (ROI) in a subject's brain and then estimates ROI source activations based on the estimated source of the ROI. It is then determined if a subject is in a bad encoding state based on the ROI source activations. Finally, one or more electrodes in the headcap are activated to apply a pulsed transcranial stimulation (tPS) therapy when the subject is in a bad encoding state, a predefined external event or behavior occurs, or the subject is in a consolidation state during sleep.

In another aspect, the one or more electrodes are activated to apply the tPS for a duration of the external event or behavior, or the bad encoding state, after which the system ceases activating the one or more electrodes.

Further, the one or more electrodes are activated to apply the tPS until the encoding state changes from bad to good.

In yet another aspect, the tPS is applied in closed loop slaved to particular phases of a source localized intracranial electroencephalography or electroencephalography waveform known to be important to a brain function of interest in the ROI of interest.

Additionally, estimating ROI source activations based on the estimated source of the ROI is performed using an inverse mapping of electroencephalography data.

In yet another aspect, estimating ROI source activations based on the estimated source of the ROI is performed or corrected using implanted electrodes.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
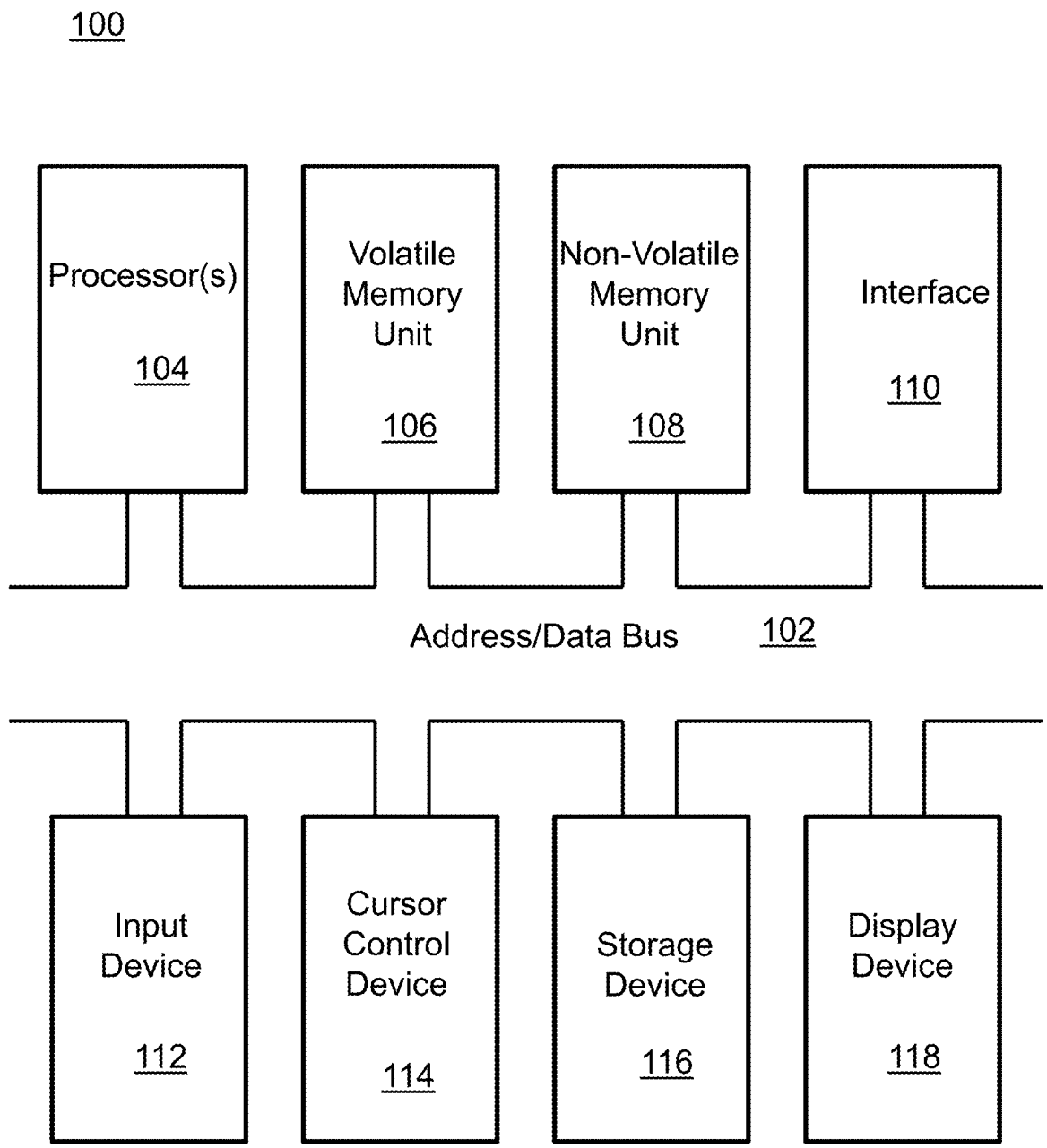
FIG. 1 is a block diagram depicting the components of a system according to various embodiments of the present invention.

The present invention relates to a transcranial stimulation system and, more specifically, to a closed-loop pulsed transcranial stimulation system for cognitive enhancement. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Jacek P. Dmochowski, LaurentKoessler, Anthony M. Norcia, MaromBikson, Lucas C. Parra (2017). Optimal use of EEG recordings to target active brain areas with transcranial electrical stimulation. NeuroImage, Vol 157, pages 69-80.
2. Y Ezzyat, J E Kragel, J F Burke, D F Levy, A Lyalenko, P Wanda, et al (2017). Direct brain stimulation modulates encoding states and memory performance in humans. Current Biology 27 (9), 1251-1258.
3. Matthew R. Krause, Theodoros P. Zanos, Bennett A. Csorba, Praveen K. Pilly, Jaehoon Choe, Matthew E. Phillips, Abhishek Datta, and Christopher C. Pack. Transcranial direct current stimulation facilitates associative learning and alters functional connectivity in the primate brain. Current Biology 27, 1-11, Oct. 23, 2017.
4. Elsa Van Der Loo, Marco Congedo, Mark Plazier, Paul Van de Heyning, Dirk De Ridder. (2007). Correlation between Independent Components of scalp EEG and intra-cranial EEG (iEEG) time series. International Journal of Bioelectromagnetism, Vol. 9, No. 4, pp. 270-275.
5. R. Hyder, N. Kamel, T. B. Tang and J. bornot, "Brain source localization techniques: Evaluation study using simulated EEG data," 2014 *IEEE Conference on Biomedical Engineering and Sciences (IECBES)*, Kuala Lumpur, 2014, pp. 942-947.
6. Jasmine Song, Colin Davey, Catherine Poulsen, Phan Luu, Sergei Turovets, Erik Anderson, Kai Li, Don Tucker, EEG source localization: Sensor density and head surface coverage, Journal of Neuroscience Methods, Volume 256, 2015, Pages 9-21, ISSN 0165-0270.
7. A. M. Dale, M. I. Sereno. Improved localization of cortical activity by combining EEG and MEG with MRI cortical surface reconstruction: a linear approach, J Cognit Neurosci, 5 (1993), pp. 62-176.
8. R. Pascual-Marqui. Standardized low resolution brain electromagnetic tomography (sLORETA): technical details. Methods Find Clin Pharmacol, 24D (2002), pp. 5-12.
9. Munsif Ali Jatoi, Nidal Kamel, Aamir Saeed Malik, Ibrahima Faye, Tahamina Begum, A survey of methods used for source localization using EEG signals, Biomedical Signal Processing and Control, Volume 11, 2014, Pages 42-52, ISSN 1746-8094.

(2) Principal Aspects

Various embodiments of the invention include three "principal" aspects. The first is a system for transcranial stimulation for cognitive enhancement. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
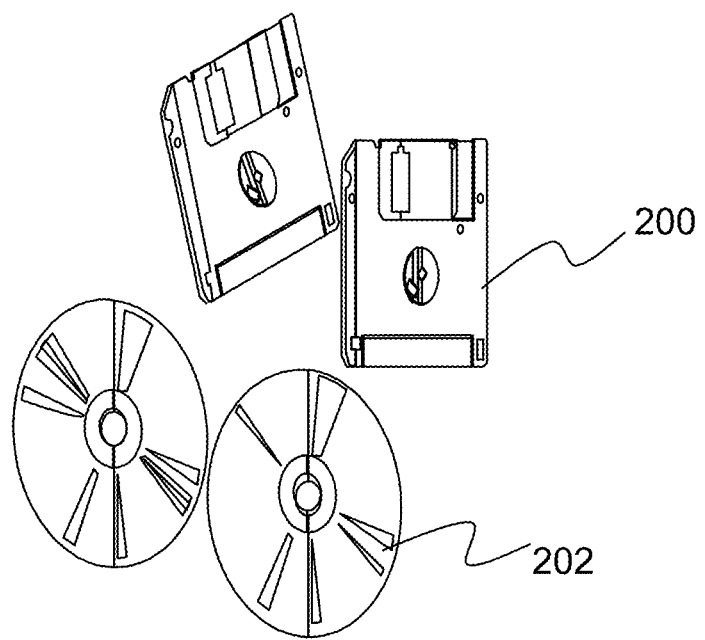
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

This disclosure is directed to a personalized closed-loop pulsed transcranial stimulation system for cognitive enhancement. The system can be used to increase the efficacy of any non-invasive stimulation techniques (including ultrasound and electromagnetic waves, such as transcranial current stimulation and transcranial magnetic stimulation) by adding brain state and/or task-aware closed-loop control of the stimulation montage (electrode placement and stimulation pattern). Depending on the requirements of different stimulation therapy montages, the stimulations may be applied during waking or sleep. In either cognitive state, the system of this disclosure controls application of the stimulation montage during identified critical events during a task of interest so that the stimulation is only applied when the brain is in a "bad encoding state" during waking, or "consolidation state" during sleep (defined below). Good and bad encoding states can be learned from data collected during memories that are recalled and forgotten eventually, respectively. The encoding or stimulation states could also be linked to the different phases of the hippocampal theta rhythm (namely, encoding and recall phases).

Figure 3:
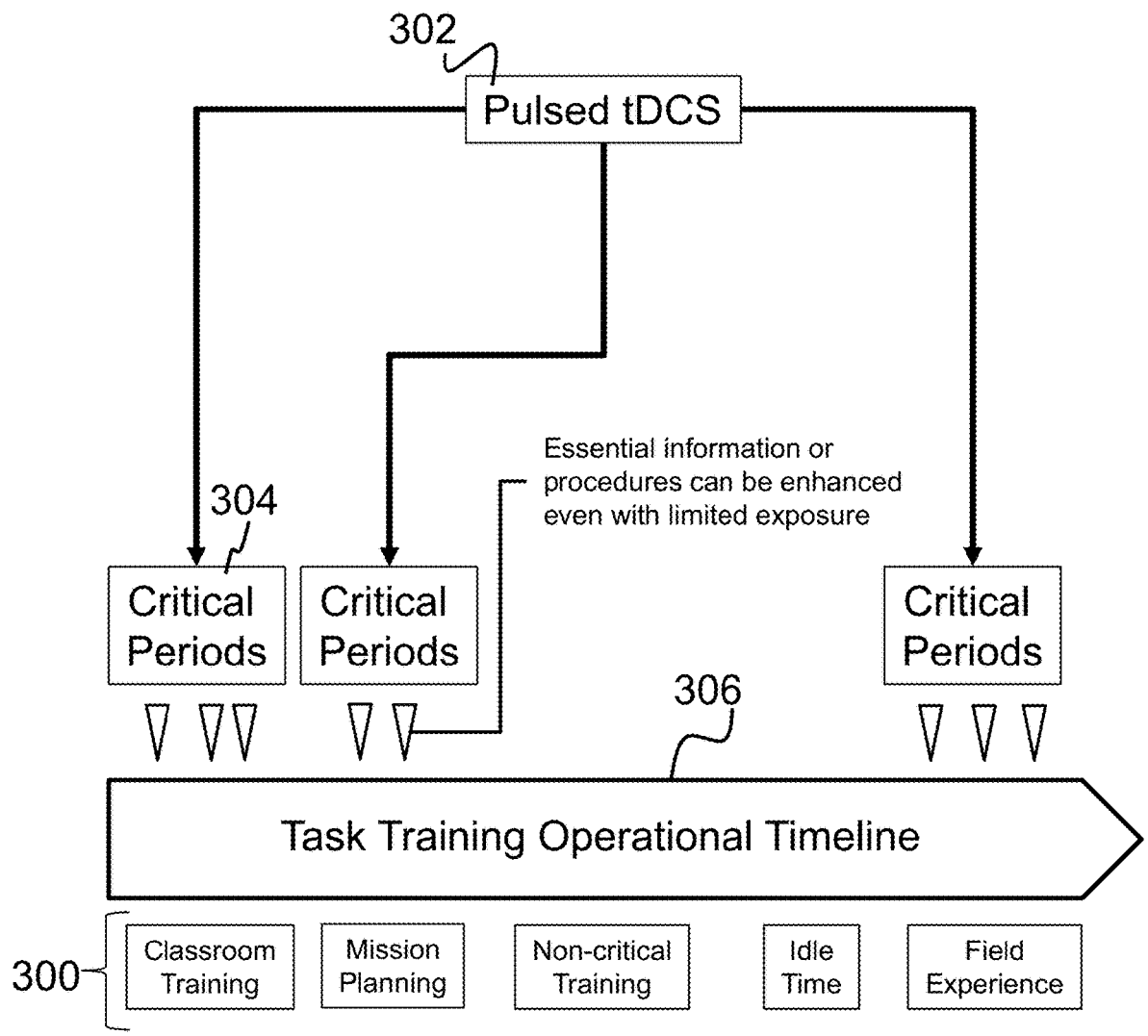
FIG. 3 is a flowchart illustrating potential applications of the system according to some embodiments of the present invention.

Pulsed transcranial stimulation could also be locked to critical segments of a task. FIG. 3, for example, illustrates potential applications 300 for the system of this disclosure, including enhancement of task performance of mission-critical information for military or other personnel, and may be targeted such that only the most critical pieces of mission/training data are strengthened over lower-priority information. Particularly, the system provides transcranial direct current stimulation (tDCS) 302 during critical periods 304 of the task training operational timeline 306 to augment experiences or memories of interest, reducing training times and accelerating domain expertise in the field. This results in a pulsed stimulation timed to match the brain state of the target region.

The system of this disclosure improves any brain-boosting or cognitive enhancement technique that is based on applying pulsed transcranial stimulation to specific regions of the brain (such as ultrasound or electrical current or magnetic stimulation, abbreviated as tPS); for example, techniques for memory consolidation enhancement, or cognitive therapy techniques for conditions like PTSD. These techniques have in common a tPS protocol for stimulating certain regions of the brain. The system described herein improves such tPS techniques by timing the tPS pulses to match times when the brain region of interest is in a "bad" encoding state, or in a consolidation state. This is in accord with recent findings, in experiments with non-human primates, that stimulation at other times is ineffective. Another advantage is that tPS stimulation is only applied when it is useful; thus, the brain is not stimulated unnecessarily during times when the stimulation is ineffective. Other techniques blindly stimulate during the whole period of a task or other time of interest. The system monitors the brain state of the regions of interest by using the standard source localization used to map transcranial electroencephalography (EEG) to voxel sources in the brain. In subjects who have implanted electrodes, this disclosure describes how to take advantage of the implants to improve the accuracy of the EEG mapping. Once the accuracy is corrected, the implanted electrode data is no longer needed. If those implants are lost or become ineffective, a transcranial EEG system still exists with much higher than normal accuracy. This is another advantage of the described approach, which can also use intracranial sensors to directly control tPS.

The system effectively enhances the efficacy of brain-boosting and cognitive enhancement systems for both normal subjects (e.g., during training) and those with learning difficulties related to skill acquisition or memory consolidation. The system can be used to enable people to reinforce episodic memories and acquire skills faster, or to gain relief from cognitive deficits such as PTSD or irrational fears, or even have more restful sleep or relaxation.

The interventions employing closed-loop HD-EEG sensing and HD-tCS stimulation according to embodiments of the present invention can be incorporated into a variety of pre-existing products, non-limiting examples of which include a) Neuroelectrics HD-tCS+Biosemi HD-EEG; b) Neuroelectrics HD-tCS+ANT Neuro HD-EEG; and c) EGI integrated 128-channel HD-EEG/tCS. These pre-existing products are non-invasive stim/sense products that correspond to commercial systems controlling currents sent to the tCS electrodes and reading data from the EEG sensors. Man-portable devices are possible even if the subject has an implanted electrode array. There may be other reasons why a subject may have an implanted array (e.g., to treat tinnitus or Parkinson's disease), and if so, that data can be used to improve the operation of the invention. However, it is not necessary to implant an array in a healthy subject to benefit from the system described herein. Thus, the present invention can be easily integrated into existing stimulation systems to improve the efficacy of tPS therapy systems and control the application of stimulation to discrete pulses timed to when they are most effective. This will reduce the power drain on man-portable implementations in the future using, for example, a non-invasive EEG sensor. An integrated brain-monitoring and transcranial stimulation system will have broad applicability in research and rehabilitation, and in new development of commercial and military applications.

(4) Specific Details of Various Embodiments

As noted above, this disclosure is directed to a personalized closed-loop pulsed transcranial stimulation system for cognitive enhancement. During operation, the system requires an accurate estimation of the activations of the brain regions that are to be stimulated, so that stimulation can be applied only when the brain is in a "bad" encoding state. In the absence of implanted electrodes, the only way to get localized activation measurements from a region of the brain is to employ a well-known technique called source localization. If implanted electrodes are available, it may be possible to get hi-fidelity data from those electrodes, yet source localization will still likely be required. Source localization is based on an inverse mapping from the electrical sources (neural membrane voltages in regions in the brain) to the activities sensed by a number of discrete electrodes. Source estimation of a ROI is known in the art. Dmochowski et al., for example, describes how to take an EEG reading and compute a tPS montage (electrode placement and activation patterns) that can target the same brain source regions (see Literature Reference No. 1).

High-Definition transcranial EEG (HD-EEG) provides electrical activities from the whole brain, but these scalp recordings are inaccurate because of difficulty maintaining leads and low impedance. That magnifies the inaccuracies of source localization. Another source of inaccuracy in inverse models is that they are based on generic models of the shape and size and conductivities of a subject's brain, and not personalized to an individual subject's brain.

Intra-cranial EEG (iEEG) solves many of the technical hurdles of scalp recording (but of course has limited scope). Impedances are low, signal quality is high, and in experienced hands complication rates are ~1% or less for implantation. With recent success of chronically implanted devices for movement disorders, and more recently for antiepileptic devices, continuous iEEG monitoring is becoming an important tool for understanding, and potentially treating, mental diseases such as epilepsy and depression, despite its relative invasiveness. Implanted sensors provide very accurate measurements, but can only sense the limited areas they are implanted in. But if the subject has such implanted electrodes, the accuracy of the source localization from the EEG array can be improved by using the Van der Loo et al. method (see Literature Reference No. 4). The Van der Loo method uses the very accurate measurements from an iEEG array to correct the source localization mapping from HD-EEG, improving the accuracy of source localization from HD-EEG for sources throughout the brain.

Figure 4:
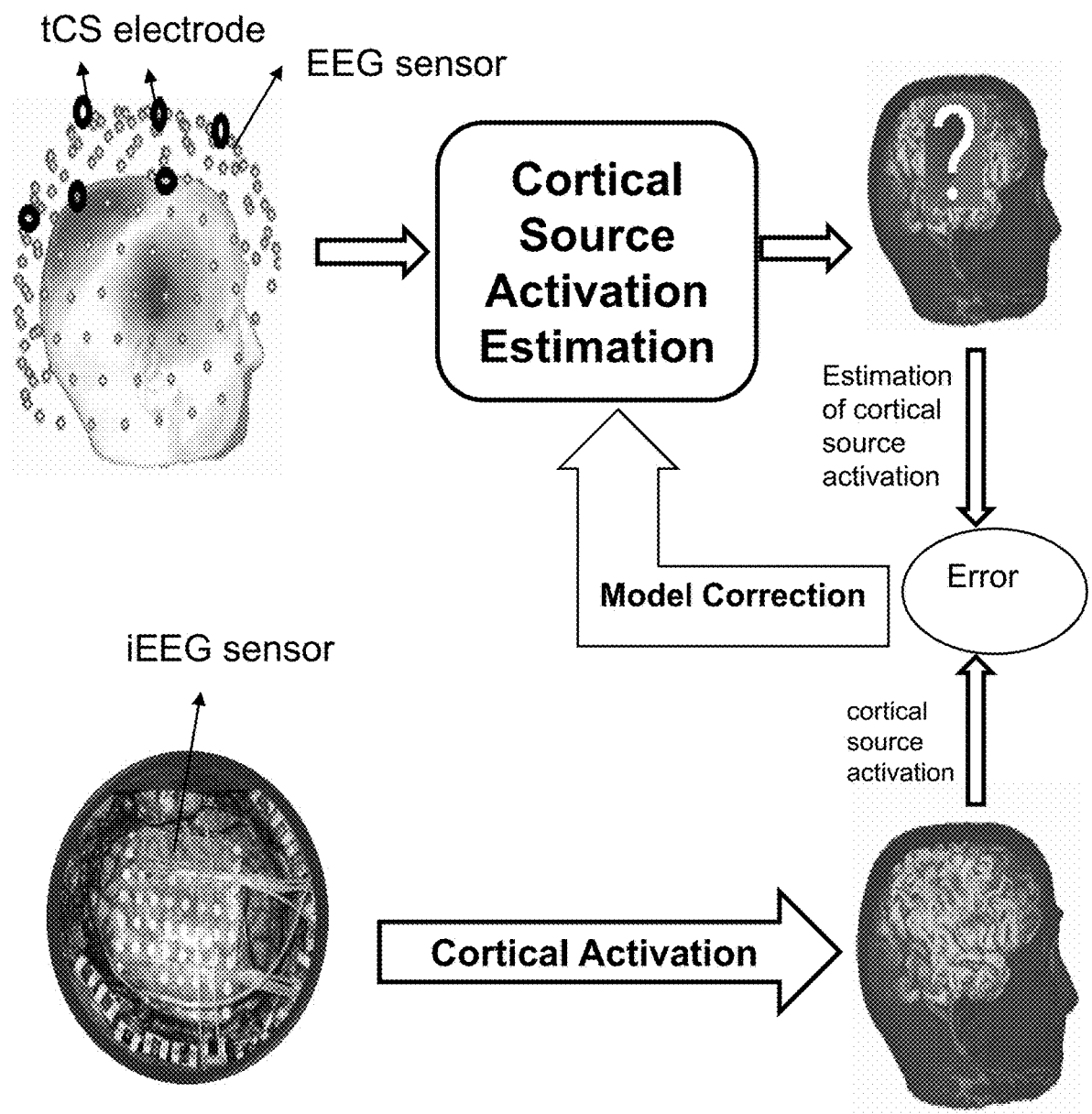
FIG. 4 is a flowchart illustrating a prior art method for transcranial stimulation.

For further understanding, FIG. 4 illustrates the Van der Loo method 400 in which the error correction is the equivalent of gradient descent. One way to implement such a correction is the following iterative algorithm:

1. Choose a set of highly activated regions sensed directly by iEEG and related to the biomarker(s) of interest.
2. For each region, use the EEG inverse model to do source localization from the EEG electrode activations.
3. Iteratively make small changes to the parameters of the inverse model to change the location of estimated neural sources until a change is found to minimize the difference with the actual location directly sensed by the iEEG array.
4. Go back to 2 and do the same for the next region. Repeat this loop until the EEG estimation of source localization matches the neural activation pattern recorded by iEEG.

In other words, the Van der Loo method 400 (see Literature Reference No. 4) does the equivalent of gradient search to correct the inverse model by comparing its estimation errors with accurate data from the iEEG sensor. The result is a personalized inverse model ("Cortical Source Activation Estimation"). If iEEG is not available, the standard method is used. The standard method would be simply performing Cortical Source Activation Estimation 502, without the benefit of the Model Correction step of FIG. 4. There are many approaches to such a "standard method". For example, a reference to a survey on methods using the standard method can be found in Literature Reference No. 9.

The system of this disclosure improves upon the prior art by providing a closed-loop control technique that ensures that stimulation is applied only when the targeted brain regions are most receptive to it (i.e., most able to learn). The location of the multiple voxels in the targeted brain regions of interest, or ROI, will vary depending on the goal of the tPS therapy. Source estimation is used to determine single-site and multi-site tCS settings that are optimal for matching known biomarkers of successful task performance. Consider the ROI to be a set of voxels in the three-dimensional (3D) volume of the brain that are to be stimulated. The ROI can include voxels from areas such as frontal, parietal, occipital, temporal cortex, or hippocampus. A "bad encoding state" during waking is one with high spectral power in lower (e.g., theta) frequency bands, and low spectral power in higher frequency bands (e.g., gamma).

Figure 5:
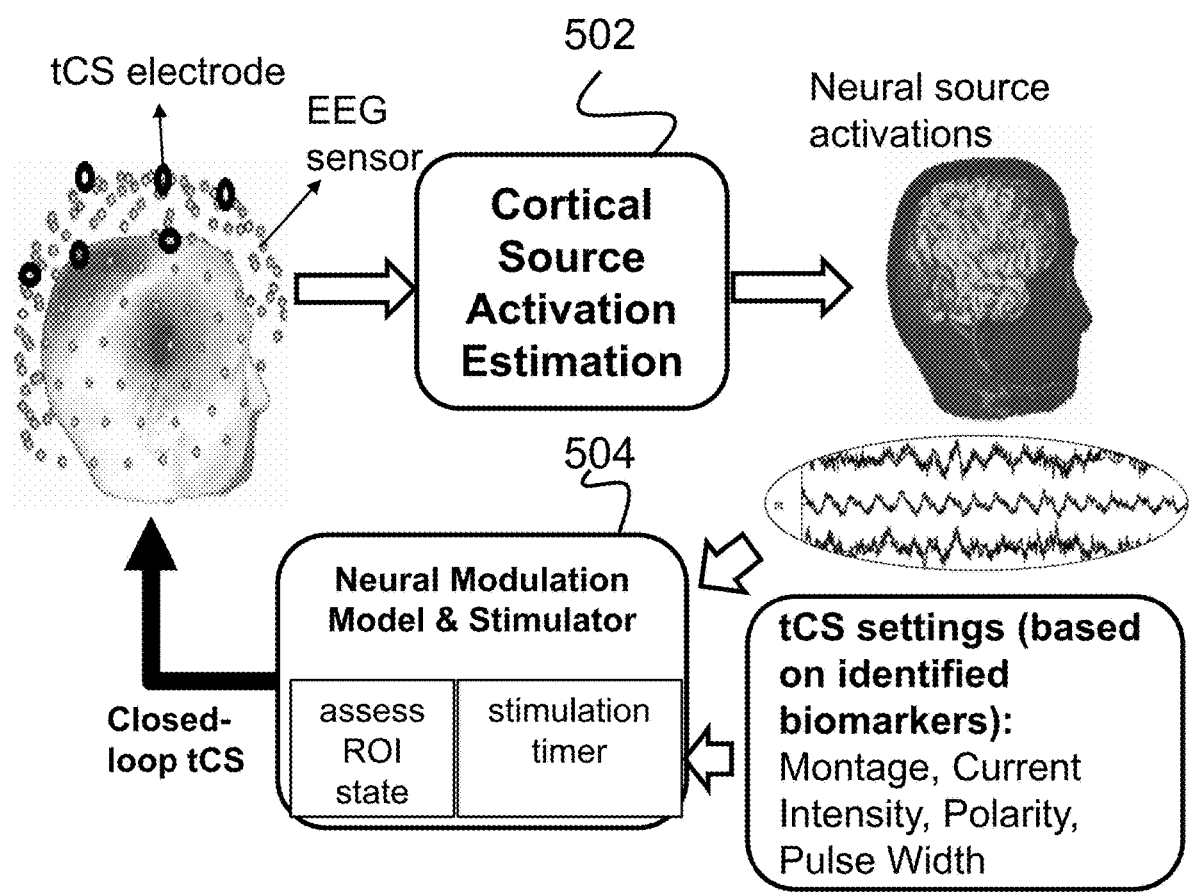
FIG. 5 is a flowchart illustrating a process for transcranial stimulation according to some embodiments of the present invention.

FIG. 5 provides a flowchart illustrating the transcranial stimulation process 500 according to various embodiments of the present application (using tCS as an example; although the same technique can be used with transcranial magnetic stimulation (TMS) or other stimulation modalities). The neural source activation patterns are estimated based on EEG data read from transcranial EEG sensors, using source localization methods applied in 502, corrected by the methods of FIG. 4 if an implanted iEEG array is available. Then biomarkers related to brain processes of interest are identified and extracted, and tCS parameters such as (but not limited to) montage, current intensity, polarity, and pulse width are set. Then the parameters are employed by the neural modulation model 504 to control application of the desired tPS montage in closed loop, to increase the efficacy of the therapy or application(s) of interest. The illustration uses tCS as an example, but TMS can be controlled in the same manner. It should be noted that the invention and method described herein is not limited to an implanted iEEG array and can also be implemented using a transcranial stimulation/EEG head cap.

Figure 6:
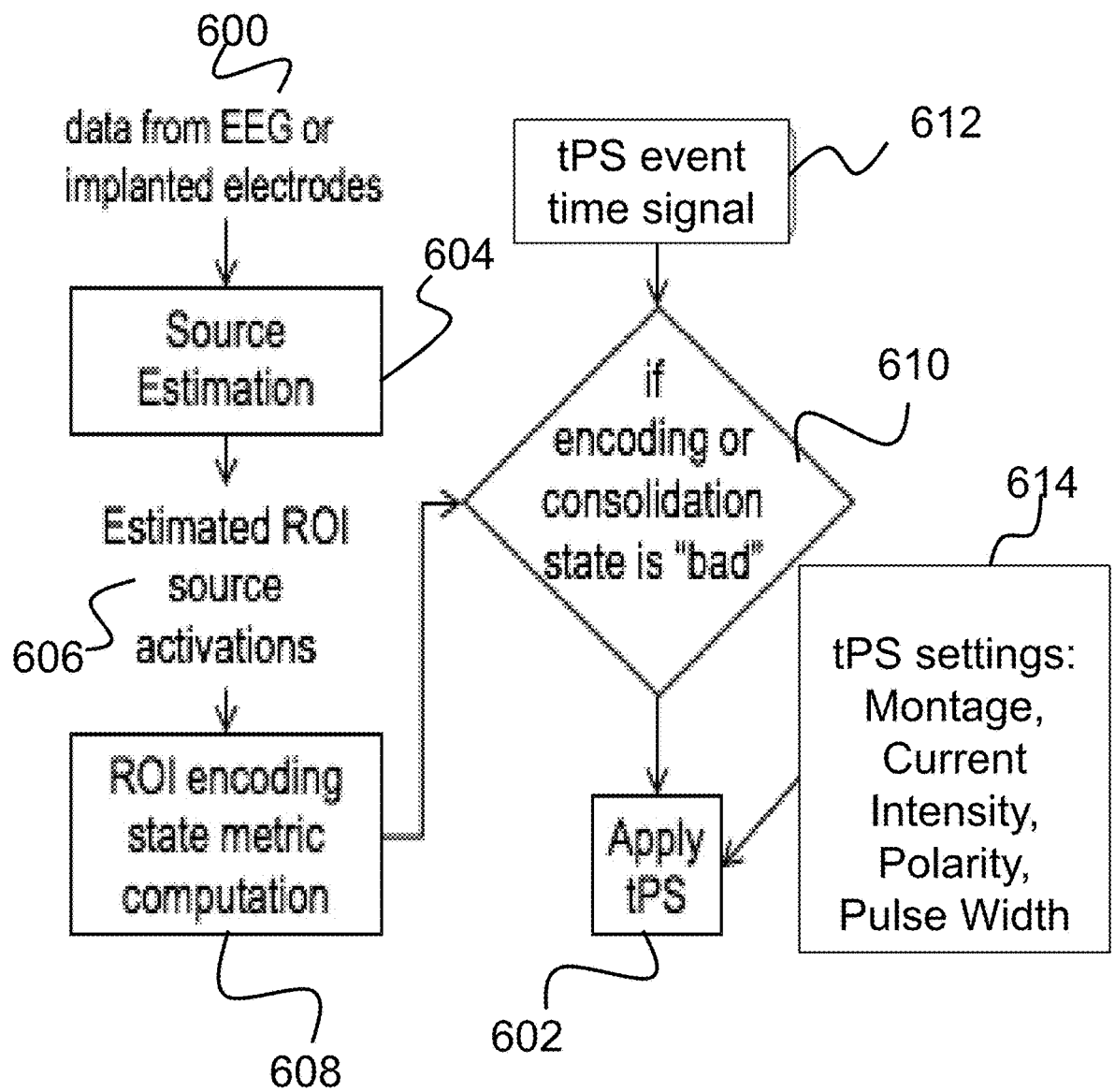
FIG. 6 is a flowchart illustrating a process for transcranial stimulation according to some embodiments of the present invention.

For further understanding, FIG. 6 is a flowchart illustrating data flow from source estimation through application of the montage. Encoding state or biomarkers in the region of interest (ROI) is computed continually. The subject can be placed in whatever environmental conditions are required to apply the tPS therapy. As shown in FIG. 6, during the time of the therapy, real-time EEG 600 is monitored from the subject, and the state assessment is made, resulting in application of a pulsed transcranial stimulation (tPS) 602 when appropriate.

Upon receiving the EEG data 600, the system generates a source estimation 604 of a ROI by employing a prior art method, such as those described Literature Reference Nos. 5 and 6. The source estimation process 604 results in the estimated ROI source activations 606. For example, source activation 606 of the ROI is computed using the minimum norm (MN (see Literature Reference No. 7)) and Standardized Low Resolution Brain Electromagnetic Tomography (sLORETA (see Literature Reference No. 8)) linear inverse source estimation methods, but if iEEG sensor(s) is/are available, this inverse mapping can be improved by identifying a mapping between iEEG and EEG and consequently minimizing the difference between the reconstructed signals from them. Alternatively, source activation 606 of the ROI can be done with implanted electrodes, if they are available.

ROI encoding of state metric computations 608 is then performed by estimating the power spectral density and other local features (e.g., phase in different frequency bands) of each ROI, as well as inter-ROI features such as coherence (or synchrony) in different frequency bands, and comparing them to the descriptions of "good" and "bad" encoding states as described below. In other words, the system determines if the subject is in a "good" or "bad" encoding state.

Whenever the state reaches a "bad" encoding state 610, and the tPS therapy regimen signals that the external event or behavior is occurring (a positive event time signal 612), the "Apply tPS" 602 module applies the stimulation (i.e., activates the electrodes) to the subject according to the tPS settings 614 of the therapy. Non-limiting examples of the external event or behavior include critical periods of a task 304, when essential information or procedures can be learned most effectively during the operational timeline of task training 300 (as illustrated in FIG. 3). The stimulation will normally be applied for the duration of the event time signal, but another possibility is to turn it off if the encoding state turns "good". For example, when real-time power spectral density of the ROI in a higher frequency band rises above a threshold, the tPS settings are turned off.

Figure 7:
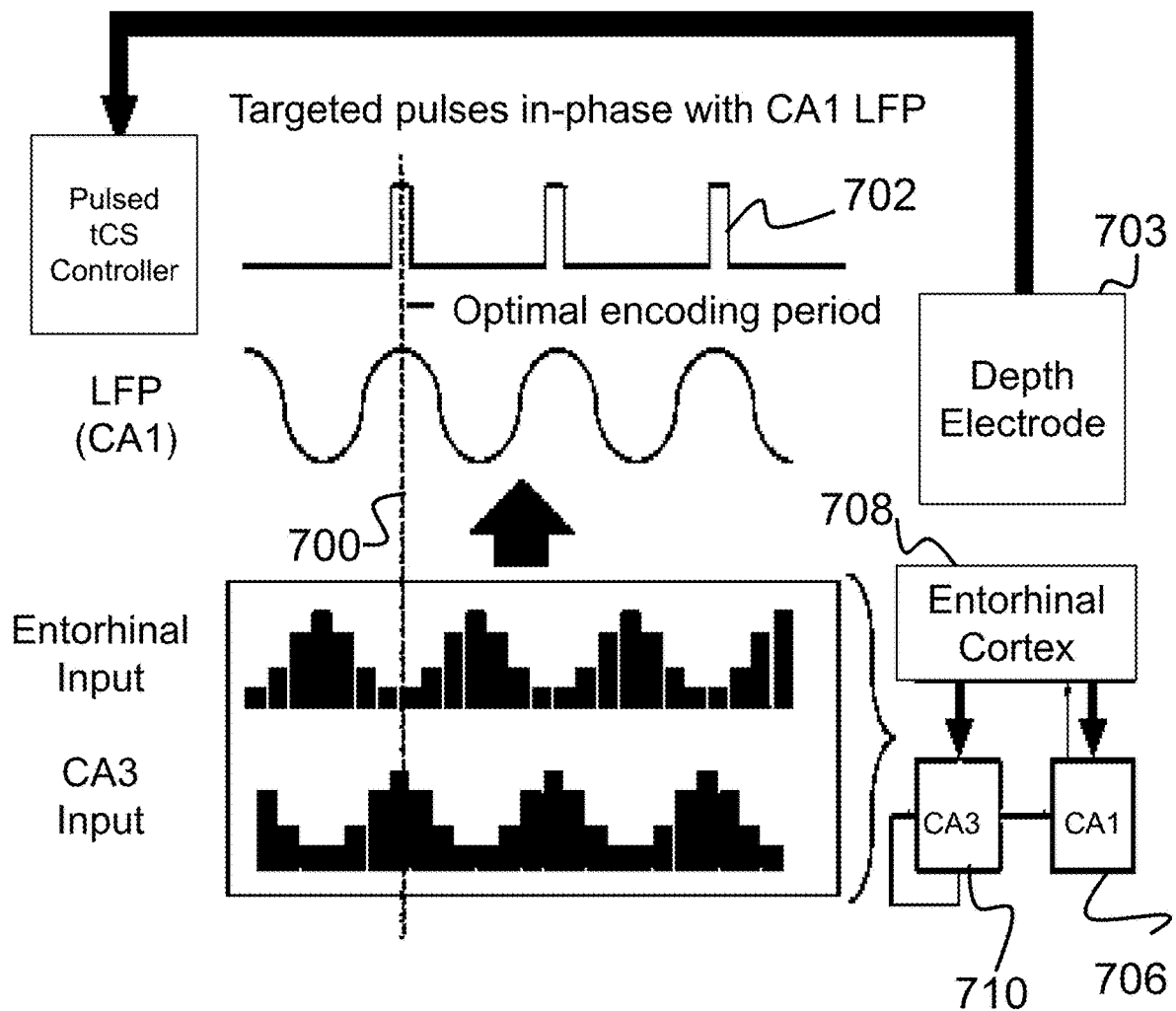
FIG. 7 is an illustration depicting that data from an implanted depth electrode could identify the encoding period of the theta rhythm, in which the underlying hippocampal circuitry allows effective encoding of new associations while simultaneously preventing interference from prior associations.

The system employs any suitable technique to define a "bad" encoding state. The definition of a "bad" encoding state may be dependent on the regimen. For example, in the work of Ezzyat et al. (see Literature Reference No. 2), such a state was defined by decreased high-frequency power in wide-spread brain areas including the frontal, temporal, and parietal cortex. The power is assessed during a short trailing window (~100 ms). In the work of Krause et al. (see Literature Reference No. 3), the bad encoding state is defined as high coherence between cortical areas in low frequencies and low coherence between cortical areas in high frequencies. In FIG. 7, tPS pulse application 700 is effectively applied at the encoding (as opposed to recall) phase of a brain rhythm (e.g., the hippocampal theta rhythm). Here, targeted pulses of tPS 702 are applied using an electrode 703 during the encoding phase of the local field potential (LFP) 704 of the CA1 area of the hippocampus in order to improve memory encoding. The CA1 706 is energized by the entorhinal cortex 708 (an input to the hippocampus) and the CA3 region 710 of hippocampus, which is an associative memory storage area. Provided above is an example of a very particular brain state that is important in task-related memory encoding, which can be targed using the present invention with these pulsed transcranial interventions (tPS) 702.

Referring again to FIG. 3, an event time signal will be supplied by the tPS regimen during waking, identifying when the critical events 302 of a task 300 or behavior are occurring. The system described herein will regard this signal as a request to apply stimulation, if the brain is in a "bad" encoding state. During sleep, the memory consolidation state (positive half-waves of NREM slow-wave oscillations) is of more interest.

Figure 8:
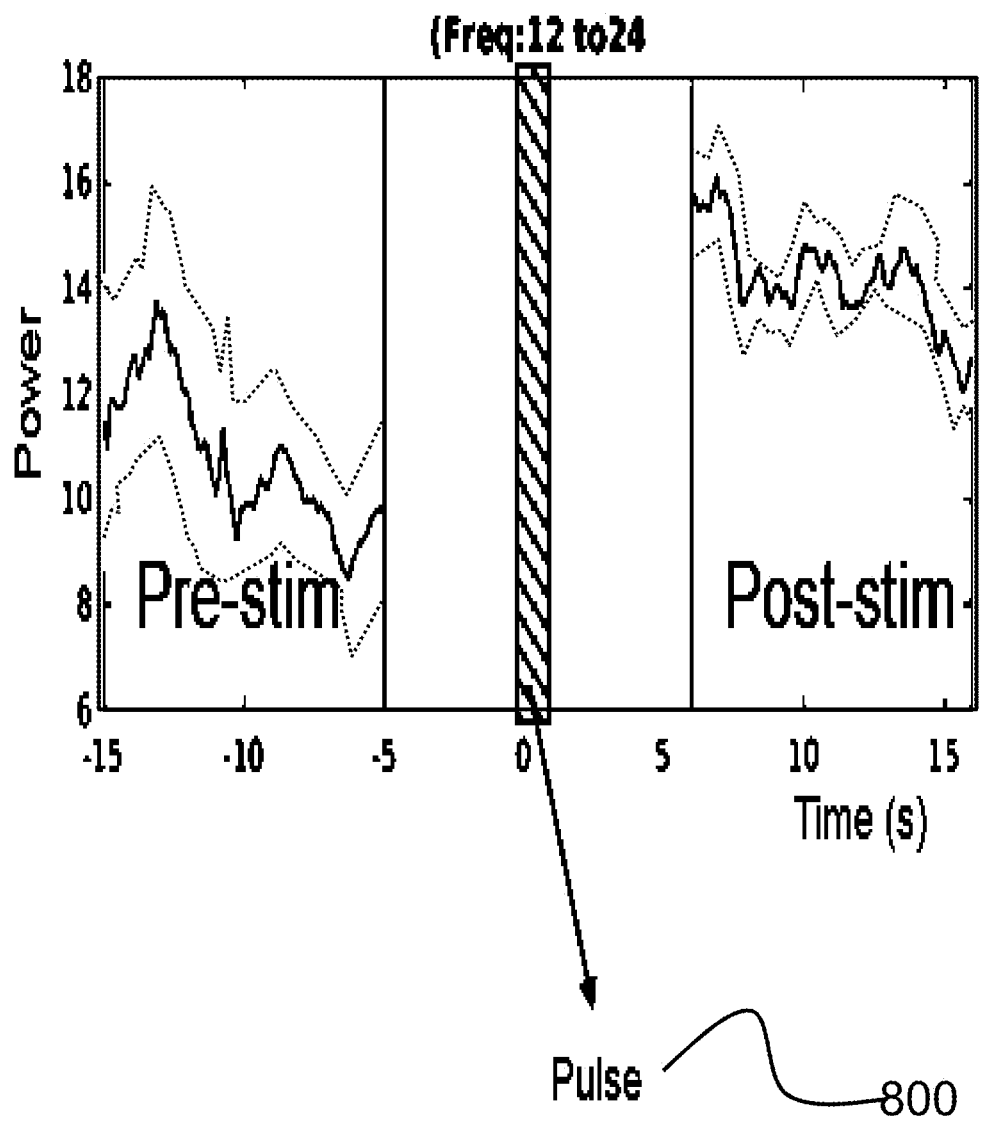
FIG. 8 is an illustration depicting that even short pulses of transcranial current stimulation elicit significant neural modulation in deep brain structures like hippocampus.

As shown in FIG. 8, experimental results in a non-human primate study show that the present method using short pulses 800 applied to brain regions when they are at such a bad encoding state cause effective and significant neural modulation. Thus, the system described herein improves the efficacy of the stimulation therapy and avoids stimulating the brain at times when it cannot benefit from the therapy.

(5) Control of a Device.

Figure 9:
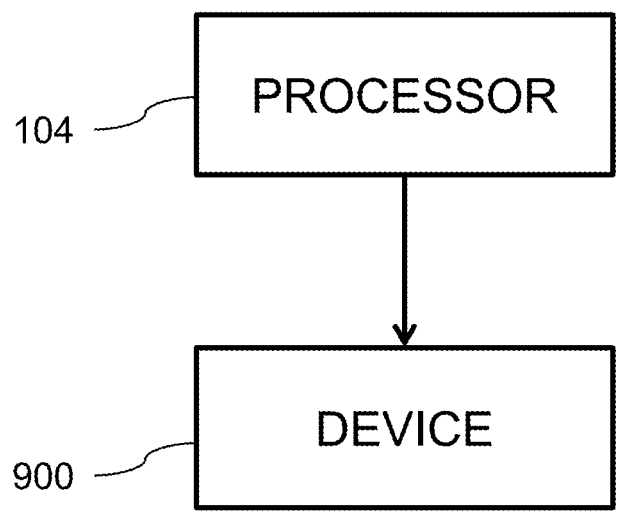
FIG. 9 is a block diagram depicting control of a device according to various embodiments.

As shown in FIG. 9, a processor 104 may be used to control a device 900 (e.g., activate electrodes) based on determining when to apply the tPS. The device 900 is any suitable device that can used to provide a transcranial stimulation to a subject, non-limiting examples of which include electrical stimulation electrodes, a magnetic field, or ultrasound. Thus, in this example, the processor 104 activates the device(s) 900 (electrodes) based on the process described herein to provide transcranial stimulation to the subject. As a non-limiting example and as referenced above, the device 900 can be an implanted iEEG array and/or a transcranial stimulation/EEG head cap. For example, FIG. 10 is an illustration of a headcap 1000 according to various embodiments of the present invention.

Figure 10:
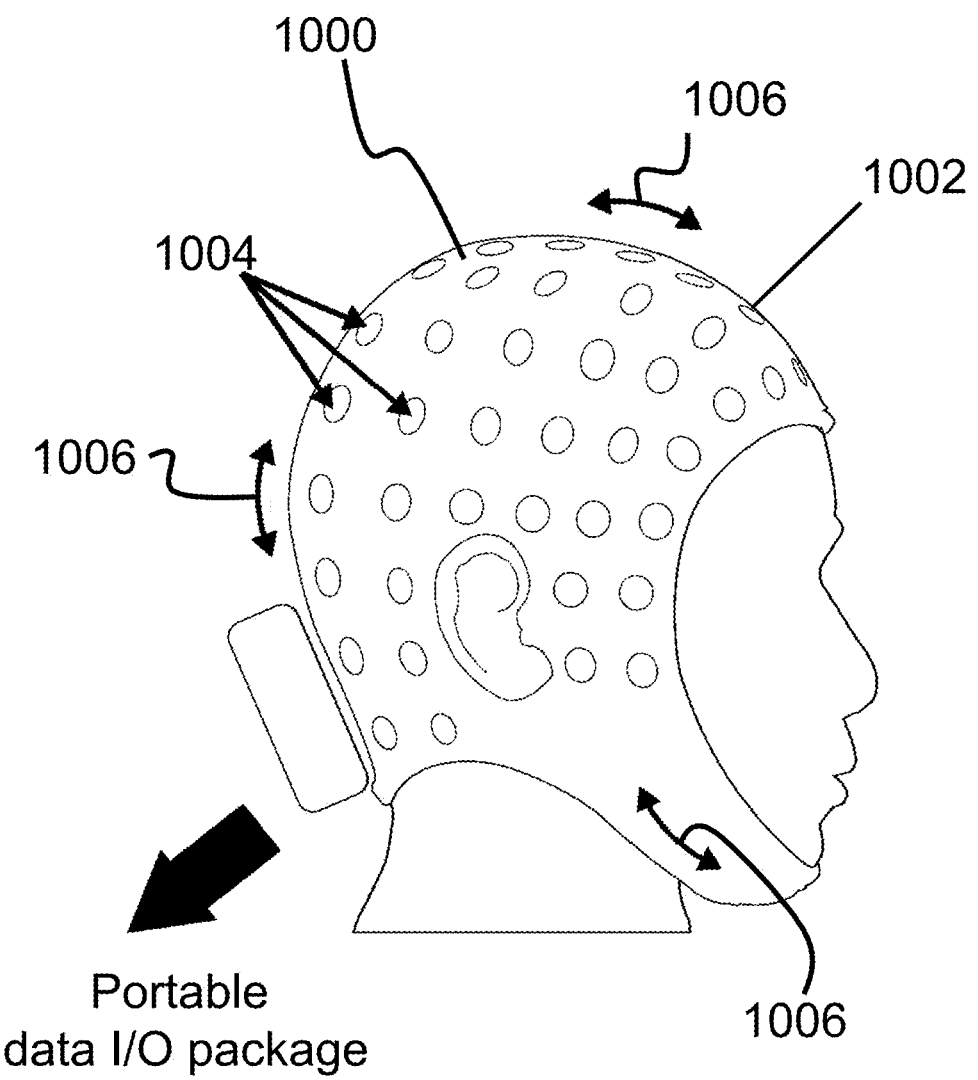
FIG. 10 is an illustration of a headcap according to various embodiments of the present invention.

As depicted in the example shown in FIG. 10, the subject may subjected to neurological stimulation via headgear, such as a headcap 1000 containing one or both of: 1) sensors 1002 to detect high-resolution spatiotemporal neurophysiological activity (e.g., EEG data); and 2) a montage of stimulation elements 1004 (i.e., electrodes) that can be used to direct current flow to specific cortical subregions. It should be understood that additional headgear configurations can also be implemented so long as they include the sensors and stimulation elements, additional non-limiting examples include a non-elastic headcap, nets (such as hair or head nets), bands, visors, helmets, or other headgear, etc.

In some embodiments, the headcap 1000 is formed of an elastic material containing sensing components that record neurophysiological activity via electrical potentials on the scalp (electroencephalogram (EEG)) and backscattered near infrared light detecting cortical bloodflow (functional near-infrared spectroscopy, FNIRS). In some embodiments, both sensors are desirably present in the cap in order to delineate cortical activity at high spatial and temporal resolution, and the headcap is elastic (compression fitting 1006) to fixate the sensitive recording elements to ensure the procurement of clean, artifact-free signals to feed the system (and to provide for sensor and stimulator consistency). Stimulation elements 1004 are also present in the same headcap 100 device, which includes multiple sets of surface electrodes which are precisely controlled to direct currents through the scalp and interstitial tissues to cortical regions of interest (high-definition transcranial current stimulation (HD-tCS)). In some embodiments, these stimulation elements 1004 maintain consistent electrical environments—particularly impedance values—in order to provide appropriate stimulation throughout cognitive enhancement. The control software (i.e., the system as described herein) of the electrodes also enables the modification of the injected electrical current, as varying stimulation protocols can be leveraged to achieve differential effects to neurological tissue. In the same vein, the headcap 1000 itself in some embodiments is configurable—that is, the headcap 1000 is constructed such that all sensing and recording components have modular configurability to allow recordings to be taken from diverse areas of the scalp, and stimulation to be applied to a wide array of brain structures. For example, the headcap 1000 is depicted as having a plurality of configurable harness locations for receiving a sensor 1002 and/or stimulator 1004. The sensors 1002 and stimulators 1004 can be formed and combined in a single harness for attaching at a harness location or they can be separately attached. The sensors 1002 and stimulators 1004 may also be spring-loaded to maintain sufficient contact with the wearer's skin. For various embodiments, one, some, or all of these components are present in the headcap 1000, and these characteristics of the device are helpful for the application of transcranial stimulation for cognitive enhancement.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for closed-loop pulsed transcranial stimulation for cognitive enhancement, the system comprising:
    a headcap having a plurality of electrodes;
    one or more processors and a memory, the memory being a non-transitory computer-readable medium having executable instructions encoded thereon, such that upon execution of the instructions, the one or more processors perform operations of:
    identifying a region of interest (ROI) in a subject's brain;
    estimating ROI source activations based on the estimated source of the ROI;
    determining if a subject is in a first encoding state based on the ROI source activations; and
    activating one or more electrodes in the headcap to apply a pulsed transcranial stimulation (tPS) therapy when the subject is in the first encoding state, a predefined external event or behavior occurs, or the subject is in a consolidation state during sleep.

2. The system as set forth in claim 1, wherein the one or more electrodes are activated to apply the tPS for a duration of the external event or behavior, or the first encoding state, after which the system ceases activating the one or more electrodes.

3. The system as set forth in claim 2, wherein the one or more electrodes are activated to apply the tPS until the encoding state changes from the first encoding state to a second encoding state.

4. The system as set forth in claim 3, wherein the tPS is applied in closed loop slaved to particular phases of a source localized intracranial electroencephalography or electroencephalography waveform.

5. The system as set forth in claim 4, wherein estimating ROI source activations based on the estimated source of the ROI is performed using an inverse mapping of electroencephalography data.

6. The system as set forth in claim 1, wherein the one or more electrodes are activated to apply the tPS until the encoding state changes from the first encoding state to a second encoding state.

7. The system as set forth in claim 1, wherein the tPS is applied in closed loop slaved to particular phases of a source localized intracranial electroencephalography or electroencephalography waveform.

8. The system as set forth in claim 1, wherein estimating ROI source activations based on the estimated source of the ROI is performed using an inverse mapping of electroencephalography data.

9. A computer program product for closed-loop pulsed transcranial stimulation for cognitive enhancement, the computer program product comprising:
a non-transitory computer-readable medium having executable instructions encoded thereon, such that upon execution of the instructions by one or more processors, the one or more processors perform operations of:
identifying a region of interest (ROI) in a subject's brain;
estimating ROI source activations based on the estimated source of the ROI;
determining if a subject is in a first encoding state based on the ROI source activations; and
activating one or more electrodes in a headcap to apply a pulsed transcranial stimulation (tPS) therapy when the subject is in the first encoding state, a predefined external event or behavior occurs, or the subject is in a consolidation state during sleep.

10. The computer program product as set forth in claim 9, wherein the one or more electrodes are activated to apply the tPS for a duration of the external event or behavior, or the first encoding state, after which the computer program product ceases activating the one or more electrodes.

11. The computer program product as set forth in claim 10, wherein the one or more electrodes are activated to apply the tPS until the encoding state changes from the first encoding state to a second encoding state.

12. The computer program product as set forth in claim 11, wherein the tPS is applied in closed loop slaved to particular phases of a source localized intracranial electroencephalography or electroencephalography waveform.

13. The computer program product as set forth in claim 12, wherein estimating ROI source activations based on the estimated source of the ROI is performed using an inverse mapping of electroencephalography data.

14. The computer program product as set forth in claim 9, wherein the one or more electrodes are activated to apply the tPS until the encoding state changes from the first encoding state to a second encoding state.

15. The computer program product as set forth in claim 9, wherein the tPS is applied in closed loop slaved to particular phases of a source localized intracranial electroencephalography or electroencephalography waveform.

16. The computer program product as set forth in claim 9, wherein estimating ROI source activations based on the estimated source of the ROI is performed using an inverse mapping of electroencephalography data.

17. A computer implemented method for closed-loop pulsed transcranial stimulation for cognitive enhancement, the method comprising an act of:
causing one or more processers to execute instructions encoded on a non-transitory computer-readable medium, such that upon execution, the one or more processors perform operations of:
identifying a region of interest (ROI) in a subject's brain;
estimating ROI source activations based on the estimated source of the ROI;
determining if a subject is in a first encoding state based on the ROI source activations; and
activating one or more electrodes in a headcap to apply a pulsed transcranial stimulation (tPS) therapy when the subject is in the first encoding state, a predefined external event or behavior occurs, or the subject is in a consolidation state during sleep.

18. The method as set forth in claim 17, wherein the one or more electrodes are activated to apply the tPS for a duration of the external event or behavior, or the first encoding state, after which the method ceases activating the one or more electrodes.

19. The method as set forth in claim 17, wherein the one or more electrodes are activated to apply the tPS until the encoding state changes from the first encoding state to a second encoding state.

20. The method as set forth in claim 17, wherein the tPS is applied in closed loop slaved to particular phases of a source localized intracranial electroencephalography or electroencephalography waveform.

21. The method as set forth in claim 17, wherein estimating ROI source activations based on the estimated source of the ROI is performed using an inverse mapping of electroencephalography data.

* * * * *